United States Patent
Singh et al.

(10) Patent No.: US 11,318,092 B2
(45) Date of Patent: May 3, 2022

(54) NUTRITIONAL COMPOSITIONS FOR THE MANAGEMENT OF HYPONATREMIA

(71) Applicant: NEPHCENTRIC, LLC, Phoenix, AZ (US)

(72) Inventors: Bhupinder Singh, Phoenix, AZ (US); Lee Souders, Albuquerque, NM (US)

(73) Assignee: NEPHCENTRIC, LLC, Phoenix, AZ (US)

( * ) Notice: Subject to any disclaimer, the term of this patent is extended or adjusted under 35 U.S.C. 154(b) by 0 days.

(21) Appl. No.: 17/063,327

(22) Filed: Oct. 5, 2020

(65) Prior Publication Data

US 2021/0100743 A1  Apr. 8, 2021

Related U.S. Application Data

(60) Provisional application No. 62/910,142, filed on Oct. 3, 2019.

(51) Int. Cl.

| | |
|---|---|
| *A61K 9/00* | (2006.01) |
| *A61K 31/17* | (2006.01) |
| *A61K 31/715* | (2006.01) |
| *A61K 47/12* | (2006.01) |
| *A61K 47/26* | (2006.01) |
| *A61K 33/06* | (2006.01) |

(52) U.S. Cl.
CPC ............ *A61K 9/0095* (2013.01); *A61K 31/17* (2013.01); *A61K 31/715* (2013.01); *A61K 33/06* (2013.01); *A61K 47/12* (2013.01); *A61K 47/26* (2013.01); *A61K 9/0053* (2013.01)

(58) Field of Classification Search
CPC .... A61K 9/0095; A61K 31/17; A61K 31/715; A61K 47/12; A61K 47/26; A61K 33/06; A61K 9/0053; A61K 31/718; A61K 47/36; A61K 47/02; A23L 29/294; A23L 33/10; A23L 33/125

See application file for complete search history.

(56) References Cited

U.S. PATENT DOCUMENTS

| | | | | |
|---|---|---|---|---|
| 3,947,596 | A | * | 3/1976 | Cannalonga ........... A61K 9/143 514/725 |
| 2010/0226994 | A1 | * | 9/2010 | Hirai ...................... A61K 31/22 424/490 |
| 2015/0142074 | A1 | | 5/2015 | Bar-Yoseph et al. |
| 2015/0351443 | A1 | | 12/2015 | Strozier et al. |

FOREIGN PATENT DOCUMENTS

WO  2014153044 A1  9/2014

OTHER PUBLICATIONS

Decaux, Urea treatment Hyponatremia Clin. Med. Sept, p. 1043 (Year: 2014).*
International Search Report received in Application No. PCT/US20/54283 dated Jan. 29, 2021, 2 pages.
Rondon-Berrios, et al., "Urea for the Treatment of Hyponatremia," American Society of Nephrology, vol. 13, Nov. 13, 2018, 13 pages.
Written Opinion received in Application No. PCT/US20/54283 dated Jan. 29, 2021, 5 pages.

* cited by examiner

*Primary Examiner* — Matthew P Coughlin
*Assistant Examiner* — Thurman Wheeler
(74) *Attorney, Agent, or Firm* — Jeff B. Vockrodt; Culhane Meadows, PLLC

(57) ABSTRACT

The present invention involves novel urea compositions for oral administration, that are useful for treatment or management of hyponatremia. Also disclosed are novel methods of making the urea compositions.

5 Claims, No Drawings

NUTRITIONAL COMPOSITIONS FOR THE MANAGEMENT OF HYPONATREMIA

FIELD OF THE INVENTION

This invention relates to novel urea compositions for oral administration that are useful for treating or managing hyponatremia. Also disclosed are novel methods of making the urea compositions.

BACKGROUND OF THE INVENTION

Hyponatremia is an electrolyte abnormality with a potential for significant morbidity and mortality. The condition arises when a person exhibits a positive balance of water with or without a deficit of sodium, which is recognized when the plasma sodium falls below the level of 135 mmol/L. Hyponatremia can occur in isolation in individuals who over-consume water. But more frequently hyponatremia results from a complication of medication or other underlying medical conditions leading to a diminished excretion of water.

Hyponatremia may lead to water intoxication, which results from retention of excess water causing the normal tonicity of extracellular fluid to fall below the safe limit. This may result in a potentially fatal disturbance in brain function. Typical symptoms of water intoxication include nausea, vomiting, headache, and malaise. Because nausea may also release anti-diuretic hormone (ADH), which causes water retention, this may cause a positive feedback loop that further worsens the symptoms of hyponatremia. Upon worsening conditions, a patient may experience reduced reflexes, convulsions, stupor, coma, or even death.

One way of treating hyponatremia is to administer urea to the patient. See, for example, 2014 European Society of Endocrinology, European Society of Intensive Care, European renal Association-EDTA. While the benefits of oral administration of urea are well documented, challenges exist in the development of an oral urea product that is acceptable for patients. Problems include delivering a clinically beneficial amount of urea and the undesirable organoleptic properties of urea compositions. Prior attempts to reduce the bitter taste have included using citric acid. One such composition includes urea 10 g NaHCO3 2 g+citric acid 1.5 g+sucrose 200 mg, which is to be dissolved in 50 to 100 mL water. The resulting solution, however, was found to be not very palatable. Moreover, the composition is severely degraded when exposed to humidity due to reaction of the sodium bicarbonate with the citric acid.

One product currently available on the market addressing some of these issues is sold under the tradename Ure-Na™, which is a powder form of urea. This product included 15 g urea doses. The composition included urea 15 g, maltodextrin 1.19 g, as well as natural flavor, e.g., cherry or lemon-lime. The inventors have found that the original version of Ure-Na suffers from problems including clumping and sticking during packaging. Also, the product was susceptible to caking after periods of storage.

The inventors have found a need to improve urea compositions to make them easier to manufacture, while maintaining desirable properties for their use in the treatment of hyponatremia.

SUMMARY OF THE INVENTION

In an embodiment, the invention relates to a powder composition that can be used to treat hypernatremia. The powder composition includes an an amount of urea effective for treatment of hyponatremia; a polysaccharide having a dextrose equivalent (DE) between 3 and 20; and calcium silicate, the calcium silicate having a particle size in the range of 3 to 7 microns, wherein less than 10% of the particles by weight have a diameter less than 3 microns or greater than 7 microns. The polysaccharide is preferably maltodextrine. The compositions of the invention are useful in delivering urea to patients suffering from hyponatremia, in a form that is useful for oral administration.

In one aspect the invention relates to a powder composition that includes (a) 60-80 wt % of urea; (b) 4-15 wt % maltodextrine; and (c) 2-10 wt % calcium silicate, the calcium silicate having a particle size in the range of 3 to 7 microns, wherein less than 10% of the particles by weight have a diameter less than 3 microns or greater than 7 microns.

In another aspect, the invention relates to methods of treating hyponatremia by orally administering these urea compositions. This may involve dispersing or dissolving the product in water, followed by ingestion. Alternatively, the powder may be added to food or a pre-packaged food product.

DETAILED DESCRIPTION OF THE INVENTION

The present invention can be broadly described as a more stable powder composition comprising an amount of urea effective for treatment of hyponatremia. It may also involve treating those suffering from hyponatremia, or who are at risk from developing hyponatremia, with the urea composition of the invention. The composition may be dispersed in water or another liquid before ingestion by the patient, or may be added to food. Alternatively, the composition may be added to food and packaged until it is ready for use.

The invention also relates to methods of making urea compositions that avoid manufacturing and packaging problems arising from the active ingredient, urea. The inventors have identified several difficulties in the manufacturing of a stable urea composition that arise due to the unique properties of urea, including its hygroscopic nature. For example, the processing of Ure-Na powder has been complicated by sticking of the powder and clumping of the product onto to various parts of the manufacturing and packaging machinery. This required frequent stopping the manufacturing line and cleaning of the processing equipment in order to maintain consistent product quality.

The present inventors have also found that the Ure-Na product was sometime found to cake during storage, resulting in waste of finished product. Because the general mode of administration is dispersing the powder from a sachet into water by pouring the powder into a glass and stirring, a caked product makes this more difficult. For this reason, caked product will not be used and this results in unwanted waste of the product.

Previous attempts to address these problems included the addition of calcium silicate in the manufacturing of Ure-Na. Calcium silicate is a known anti-caking agent. However, while this added calcium silicate had the advantage of improving the product, the inventors found that further modification of the composition is required. The present invention involves urea composition in a powder form that does not clump and has desirable organoleptic properties making it suitable for use in the treatment of hyponatremia.

The inventors discovered that the prior composition of Ure-Na™ would often clump during manufacturing, sticking to the machines even when humidity was controlled. This would lead to the product clumping over time. The original Ure-Na™ composition included 15 g of urea and 1.19 g of maltodextrin. This composition was altered to add calcium silicate 4.8 g in order to avoid clumping. However, the inventors still observed clumping in the final packaged product. The calcium stearate used in this composition had a mean particle size between 7-10 microns.

The inventors discovered two factors that are important to avoid clumping. First, appropriate selection of calcium silicate is important. Certain versions of calcium silicate having a larger particle sizes with an average particle diameter greater than 7 microns appear to reduce clumping to a lesser degree than particles having a diameter of 5 microns. Accordingly appropriate selection of a metal silicate such a calcium silicate having an average diameter between 3.0 and 7 microns is desired, and more preferably between 4.0 and 6.0 microns. Particles that are larger than these cutoffs take more time to disperse or dissolve in water, whereas particles below these cutoffs contribute to clumping while in the powder state.

In addition, the particle size distribution of the calcium silicate is important such that significant amounts of calcium silicate above the upper limit microns and below the lower limit is undesirable. For example, it is desirable that the particle size distribution of the calcium silicate be particularly adapted such that significant amounts below 3.0 microns, and above 7.0 microns, are avoided. Thus, it is preferred that the calcium silicate have an mean particle diameter within the range of 3.0 and 7.0 microns, and less than 10% of the particles by weight being below 3.0 micron or above 7.0 micron in diameter. In another embodiment, the calcium silicate has a mean particle diameter within the range of 4.0 and 6.0 microns, desirably a median particle size of 5.0 micron, and less than 10% of the particles by weight being below 4.0 micron and above 6.0 micron in diameter. While the threshold of 10% of particles by weight being outside the target particle diameter range is acceptable. Preferably, even lower amounts of off-target particles is desirable, such as 8%, 6%, 4%, or even 1%. For example, a composition having a mean particle diameter within the range of 4 and 6 microns, with less than 1% by weight outside of that range may be desirable.

Second, the inventors have found that increased levels of maltodextrine of 9.7% were desirable for decreasing clumping. Therefore, it is desirable to increase the level of maltodextrine to greater than 7% by weight, and more preferably between 7 and 12 wt %, and most preferably 9.7%. In one particular embodiment, the invention may be characterized by higher levels of maltodextrine (9.7% versus 6.7%), lower levels of calcium silicate (5% versus 21%), and a controlled particle size distribution for calcium silicate. Other embodiments are more broadly characterized by the ranges and amounts disclosed herein.

The inventors found a novel urea composition that does not clump while providing suitable properties for an oral urea composition. The composition preferably has between 60-80 wt %, more preferably 65-75 wt %, and most preferably about 67 wt % urea. The composition comprises preferably from 4-15 wt %, more preferably from 7-12 wt %, and most preferably about 9.7 wt % of a polysaccharide having a dextrose equivalent (DE) between 3 and 20. Preferably the polysaccharide is maltodextrin. The composition preferably comprises 2-10 wt %, more preferably 3-8 wt %, and most preferably about 5 wt % calcium silicate. The calcium silicate typically includes 99% calcium silicate, and 1% sodium sulfate by weight. The sodium sulfate therefore may be present in the urea powder composition.

EXAMPLE 1

The following ingredients were added mixer to produce a dry powder, which was then added in a dose of 15 grams to a pouch.

| Component | Amount | wt % |
|---|---|---|
| USP Urea | 15000 mg | 67.0% |
| Sucralose | 210 mg | 0.9% |
| Citric acid (anhydrous) | 1600 mg | 7.1% |
| Natural Lemon-Lime Flavor | 2300 mg | 10.3% |
| Maltodextrine M-500 | 2170 mg | 9.7% |
| Calcium Silicate (particle size 3-7 μm) | 1120 mg | 5.0% |

The composition is prepared by adding into a mixer the urea, maltodextrin, and calcium silicate. The resulting powder is free flowing a resistant to clumping. The powder composition is preferably packaged in a pouch that can be sprinkled onto food, or mixed with a liquid such as water. The composition forms a suspension when mixed with water, which allows for convenient ingestion. In this sense, the powder can be distributed and sold as a medical food. Alternatively, the powder may be incorporated into another medical food product such as a cookie or bar form similar to a diet bar.

The product of Example 1 was packaged in pouches using the same packaging used for the previous Ure-Na™ product that lacked calcium silicate. The consumer returns associated with clumping for the previous Ure-Na™ product was 1.4%. Return data for the product of Example 1 was 0.2%. Therefore, the present invention resulted in seven-fold reduction in returns due to clumping relative to existing Ure-Na™ product.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A powder composition comprising:
   (a) 60-80 wt % of urea;
   (b) 4-15 wt % maltodextrine; and
   (c) 2-10 wt % calcium silicate, the calcium silicate having a particle size in the range of 3 to 7 microns, wherein less than 10% of the particles by weight have a diameter less than 3 microns or greater than 7 microns.

2. The powder composition of claim 1, further comprising citric acid, sucralose, and a flavoring agent.

3. The powder composition of claim 1, wherein the calcium silicate particle size in the range of 4 to 6 microns, wherein less than 5% of the particles by weight have a diameter less than 4 microns or greater than 6 microns.

4. A method of treating hyponatremia comprising administering the composition of claim 1 to a patient suffering from hyponatremia.

5. The method of claim 4, wherein the composition is administered by dispersing or dissolving the composition in water prior to consumption.

* * * * *